United States Patent
Ionascu

(10) Patent No.: US 7,604,822 B2
(45) Date of Patent: Oct. 20, 2009

(54) INJECTABLE SOLUTION WITH ANTI-INFLAMMATORY EFFECT AND PROCESS FOR MANUFACTURING THE SAME

(75) Inventor: Elena Ionascu, Craiova (RO)

(73) Assignee: Imunomod S.R.L., Rome (IT)

( * ) Notice: Subject to any disclaimer, the term of this patent is extended or adjusted under 35 U.S.C. 154(b) by 1143 days.

(21) Appl. No.: 10/381,924

(22) PCT Filed: Feb. 8, 2001

(86) PCT No.: PCT/RO01/00001

§ 371 (c)(1), (2), (4) Date: Mar. 28, 2003

(87) PCT Pub. No.: WO02/49660

PCT Pub. Date: Jun. 27, 2002

(65) Prior Publication Data

US 2004/0052872 A1    Mar. 18, 2004

(51) Int. Cl.
*A61K 36/00* (2006.01)
(52) U.S. Cl. .............. 424/725.1; 424/773; 424/725
(58) Field of Classification Search ............ 424/1
See application file for complete search history.

(56) References Cited

U.S. PATENT DOCUMENTS

| | | | | |
|---|---|---|---|---|
| 3,192,048 A | * | 6/1965 | Liddiard | 426/597 |
| 5,919,460 A | * | 7/1999 | Ingram | 424/725 |
| 2002/0037836 A1 | * | 3/2002 | Henriksen | 514/2 |

FOREIGN PATENT DOCUMENTS

GB    2406790 A  *  4/2005

WO    WO 9206701 A1  *  4/1992

OTHER PUBLICATIONS

Petersen, G. et al. "Anti-inflammatory activity of a pyrrolizidine alkaloid-free extract of roots of Symphytum officiale in humans." *Planta Medica*, 1993, vol. 59, No. 7, pp. A703-A704.*
Database Biosis Online! Biosciences Information Services. Abstract of Petersen, G. et al. "Anti-inflammatory activity of a pyrrolizidine alkaloid-free extract of roots of Symphytum officinale in humans." Database accession No. PREV199497204279 XP002183471. *Planta Medica*, (1993), vol. 59, No. 7, pp. A703-A704.
Commission of the European Community Brussels Oct. 26, 1992; Annex 2. Committee for proprietary Medicinal Products, "Herbal drugs with serious risks".
Analysis, separation, and biossay of Pyrrolizidine alkaloids from comfrey (Symphytum officinale).
Imunomod Composition—Official analyses of the La Sapienza University of Rome, Vegetarian Biology Department.

* cited by examiner

*Primary Examiner*—Christopher R Tate
*Assistant Examiner*—Danah Al-Awadi
(74) *Attorney, Agent, or Firm*—Ladas and Parry LLP; Ofelia Ionascu

(57) ABSTRACT

An anti-inflammatory injectable solution is prepared from *Symphytum officinale* roots by cutting and drying of the vegetal material; calcining it at a temperature of 550-600° C., over a period of 3 to 4 hours; dissolving the ash obtained in distilled water at a ratio of 1:100 to form a solution, the obtained solution is filtered under vacuum, followed by filtration through milipor or semper filters to produce a filtrate and the filtrate is subjected to boiling evaporation to produce a liquid having a viscosity of 6.57±0.5 cP; and then drying a thin layer of the liquid so producedat a temperature of 200-250° C., over a period of 5-15 minutes until a white powder is obtained; and thereafter dissolving said white powder in distilled water in amount of 1 to 700 mg to 100 ml distilled water or saline solution.

7 Claims, No Drawings

INJECTABLE SOLUTION WITH ANTI-INFLAMMATORY EFFECT AND PROCESS FOR MANUFACTURING THE SAME

The present invention relates to an injectable solution, with anti-inflammatory effect, a process for manufacturing the same and a method for the treatment of autoimmune diseases using the said solution.

It is known that an increased number of human diseases, e.g. nephrosis, rheumatoid arthritis, dermatomyositis, chronic hepatitis, leukocytoclastic vasculitis, etc., may be designated as autoimmune disorders. It is generally acknowledged that pathophysiology of immune-complexes, i.e. an autoimmune response following viral, bacterial or parasitic aggression leads to qualitative and quantitative alterations in leukocytes named lymphocytes which are involved in the organism immune defense. An important role in restoring the immune response was proved to be played by drugs with immuno-modulating activity, which, thanks to their composition, rehabilitate the salt balance of the internal human body medium, stimulate the lymphocyte division, promote antibody synthesis and enhance the phagocytic capacity (Franco Dammaco, "Imunologia in Medicina", Edi. Ermes, Milano, 1989, p 67 cap 3.15, tab. 3.2, p 98 tab. 19.8, p 679).

Various drugs, which are obtained from medicinal herbs, with active principles having therapeutical qualities for the treatment of immunodeficiency syndrome, are known in the art. Such a product is a composition obtained in the form of a vegetal extract derived from the air segments of the *Chimaphila umbellate, Apocynum androsaemifolium, Symphytum officinale* and *Equisetum hyemale* (WO 97-04793).

The roots of *Symphytum officinale* are known to be used as external application for the treatment of hard healing wounds, proving that this plant segment has real hemostatic and healing capacities. These properties have been attributed to the allantoin content (0.6-0.8%), a toxicity-free principle (Evdochia Coiciu and Gabriel Racz, "Plante medicinale și aromatice", 1962, p 550-551). Due to these properties, the *Symphytum officinale* plant has also been used in pharmaceutical industry where, through different extraction processes, the active principles obtained have been used in various pharmaceutical forms, especially for external application, for examule emulsions for the treatment of skin disorders. The object of the extraction processes is mainly the extraction of allantoin from a polyphase fluid (WO 92-06701 and EP 0673654A1).

It comes out that, until now,*Symphytum officinale* plant has been especially exploited for the extraction of its organic active principles, e. g. allantoin and mucilage contained without any investigation of the therapeutical properties of its inorganic principles.

The technical matter the present invention solves is exactly the research achievement and ascertaining of the therapeutical effects of the inorganic constituents of the*Symphytum officinale* plant and the preparation of a drug in the form of an injectable solution to confirm the real anti-inflammatory properties this plant possesses also through its inorganic constituents.

The injectable solution according to the invention comprises 1-700 mg white powder containing water soluble inorganic salts obtained from the ash resulting from the calcination of *Symphytum officinale* roots in 100 ml distilled water or saline soultion, optionally associated with 0.1-0.2 mg lidocaine for intramuscular administration.

The active powder of inorganic salts termed IMUNOMOD contains potassium salts in the range of 36 to 52% and, stoichiometrically, comprises 43.268% potassium, 14.698% sulphur, 31.675% oxygen, 0.88% iron, 0.421% sodium, 0.265% phosphorus, 0.126% chlorine, 0.043% silicon, 0.034% magnesium, 0.012% manganese and cassiopeum traces, and up to 100% being carbon from carbonates and organic residues, for example alkali metal oxalates such as hydrated potassium oxalates.

The process for manufacturing the injectable solution consists of the following steps:

a) the cutting of the*Symphytum officinale* roots and the drying of the vegetal material;

b) the calcination of the dried vegetal material at a temperature of 550-600° C. in calcination containers known per se, over a period of 3-4 hours;

c) the ash obtained after calcination is dissolved in distilled water at a ratio of 1:100, the obtained solution is filtered under vacuum, followed by filtration through Millipore or Sempore filters and the filtrate is subjected to boiling evaporation up to a viscousness of 6.57±0.5 cP [Millipore is a registered trademark of Millipore Filler Corporation of Bedford, Massachusetts; Sempore is a trademark of Jeol (Europe) S.A];

d) a thin layer of high viscosity liquid so produced is subjected to drying at a temperature of 200-250° C. over a period of 5-15 minutes until a white powder is obtained;

e) dissolving the white powder in distilled water or saline solution, optionally associated with 0.1 mg lidocaine to prepare an injectable solution.

The method for the treatment of autoimmune diseases according to the invention involves a three step regimen administration of the intramuscular injectable solution, I. e. in the first step, the daily administration of a dose of minimum 30 mg/70 kg body weight, over a period of 10 consecutive days, then, in the second step, the administration is performed with the same dose, at an interval of 1 to 2 days, until obvious positive clinical results are obtained, afterwards one proceeds to the maintenance step of the treatment by once a week intramuscular administration, in the same dose, of the injectable solution, alternating with intravenous administration.

The medical product according to the invention has the following advantages:

- possesses anti-inflammatory activity proved by the dynamics of α 2-fraction in the blood electrophoresis, its value decreasing related with the inflammatory effect decline respectively;
- produces no allergic reaction proved by quantitative level lowering of eosinophyles established by blood cell count, and thus there is no need for previous testing, but for the injectable form containing Lidocaine (only for the Lidocaine allergical test);
- acts as a MCSF factor (Multi Colony Stimulating Factor) reestablishing to normal the levels of serum leukocytes, erithrocytes and platelets;
- its manufacturing process is very simple and reproducible for obtaining its therapeutical qualities.

Two Examples for manufacturing the injectable solution according to the invention as well as the method for treatment are presented further on.

EXAMPLE 1

The fresh harvested roots of*Symphytum officinale* are washed under water stream and subjected to cutting in pieces of about 4-5 cm. The vegetal product obtained is subjected to drying following norms known per se for the conservation of the medicinal plant roots.

1000 g cut and dried roots of *Symphytum officinale* are subjected to calcination in a temperature controlled furnace in therm-resistant porcelain containers at a temperature of 550-600° C., over a period of 3-4 hours. 250-300 g light grey ash are yield. The ash thus obtained is dissolved in distilled water at a ratio of 1:100, at room temperature, with stirring over a period of 15 minutes, in glass containers. The liquid obtained is filtered under vacuum using a Nuce filter, for removing the undissolved particles. The resulting solution is subjected again to filtration using Millipore and Sempore filters. The filtrate obtained has the following ion composition : $K^+$=36.25-44.48%; $Na^+$=1.89-2.70%; $Cl^-$ 0.18-0.36%; $HCO_3^-$=34.12-55.3%; $CO_3^{2-}$=14.71-18.9% and $SO_4^{2-}$=0.96-1.20%.

IR analyses indicated vibrations corresponding mainly to $HCO_3^-$, $CO_3^{2-}$, $OH^-$ anions and hydrogen bonds.

The obtained filtrate is subjected to boiling evaporation in Pyrex glass recipients up to a liquid viscosity of 6.57±0.5 cP. Thus obtained viscid liquid is placed on Pyrex pans in thin layer and subjected to drying at 200-250° C., over a period of 5-10 minutes, thus obtaining an easy adhesive white powder. Right after the drying, the powder is removed using stainless tools, known per se, and introduced in tight ampules because of its high hygroscopic potential.

There are obtained about 40-50 g active powder called IMUNOMOD which in IR presents vibrations at 3400, 1630, 1110, 1004, 880, 845, 700, 686, 672, 640, 625, 618 and 560, and by X-ray diffraction shows the presence of $KHCO_3$, $K_2CO_3$, $KCl$, $K_2SO_4$ and $C_4H_3KO_8.2H_2O$ (potassium oxalates hydrates) crystals. These conclusions are shown by the electron microscopic image and by the IR spectrum chart.

The stoichiometrical analyses at the electron microprobe shows the following chemical composition: K=43.268%; S=14.698%; O=31.675%; Fe=0.88%; Na=0.421%; P=0.265%; Cl=0.126%; Si=0.045%; Mg=0.034%; Mn=0.012% and up to 100% being carbon within carbonates and organic residues, such as hydrated potassium oxalates.

As a result of the X-ray microanalysis, on the JCXA-50A electron microprobe, provided with AN 10000 X-ray analyzer (lithium doped silicon type detector, cooled in a cryogenic room, at the liquid nitrogen temperature), all the elements, heavier than sodium (Na) have been detected in the IMUNOMOD active powder, and among these, cassiopeum was detected too.

The radioactivity analysis of the active powder established that it is under the admitted limit.

The thermogravimetric analysis of the IMUNOMOD active powder indicated weight losses (by decomposition) on the following temperature ranges:

loss of 2 . . . 4% from the powder weight up to 100° C.;
loss of 13 . . . 14% from the powder weight up to 185° C.;
loss of 17% from the powder weight up to 280° C.;
loss of 20% from the powder weight up to 800° C.

All the decomposition effects being endothermal, indicating decomposition processes, and almost the lack of exothermal processes (burnings), indicates a low percentage of organic compounds.

IMUNOMOD active powder is formulated as a solution by its dissolving in distilled water, in amount of 600 mg to 100 ml distilled water, with an addition of 10 ml 1% Lidocaine solution. This solution is designated to fit in 5 ml ampules for intramuscular administration and the powder/ampoule concentration is given by the minimal dose for an adult/day/70 kg body weight, so the minimum daily dose would be one 5 ml ampoule, containing 30 mg active powder.

For intravenous administration, IMUNOMOD active powder is dissolved in saline solution, in amount of 200 mg to 100 ml saline solution without Lidocaine addition. This solution is designated to fit in 15 ml ampules for intravenous administration, the active powder/ampoule concentration is also given by the minimal dose for an adult/day/70 kg body weight, that is 30 mg active powder in 15 ml intravenous injectable solution.

Thus obtained solutions are fitted in unidose ampules, in aseptic medium, and are subjected to sterilization according to Romanian Pharmacopeia, $X^{th}$ edition.

The injectable solution for adults, designated for intramuscular administration, has to contain 30 mg active powder as a unidose (a 5 ml ampoule contains 30 mg active powder).

The injectable solution for adults, designated for intravenous administration, has to contain also 30 mg active powder as a unidose (a 15 ml ampoule contains 30 mg active powder).

The method for the treatment of chronic inflammatory diseases with injectable solution, according to the invention, presumes intramuscular and intravenous administration of the product concordant with a regimen of the following steps: in the first step, the daily administration, over a period of 10 consecutive days, then, in the second step, the administration is performed with an interval of 1-2 days, until obvious positive clinical results are obtain, afterwards one proceeds to the maintenance step of the treatment by once a week intramuscular administration, alternating with intravenous administration of the injectable solution.

The minimal dose for intramuscular administration to an adult is of 30 mg/day/70 kg body weight, i.e. the administration of one 5 ml ampoule.

For intravenous administration, the minimal dose is also of 30 mg/day/70 kg body weight, that is the administration of one 15 mi ampoule. Note that intravenous administration of the injectable solution according to the invention is performed very slowly, over a period of minimum 10 minutes, thanks to a very good tolerance of the injectable solution to slow administration.

The method of treatment may be applied for chronic autoimmune inflammatory diseases, such as nephrosis, rheumatoid arthritis, dermatomyositis, leukocytoclastic vasculitis, myasthenia gravis, ulcer-hemorrhagic recto colitis, autoimmune chronic hepatitis.

In the case of nephrosis, the injectable solution administration, according to the invention, is initially performed simultaneously with corticosteroid therapy, at least over a period of 10 days during the time the injectable solution according to the invention is administrated daily. In the second step of the method for treatment according to the invention, as soon as the positive effects occur (the edema retraction and the improvement of the $\alpha 2$-fraction level in electrophoresis), a slow decrease of the daily cortisone dose will be started, up to the total cortisone excretion over a period of about 3-4 months, during which the injectable solution is administrated weekly. At the end of the 4 months of treatment a notable edema retraction, along with the body weight loss, and electrophoresis correction are noticed.

In the case of arthritis, carrying out the method for treatment according to the invention, leads to joint pain relieve, decreasing and normalizing the values of the following analyses: ESR, reactive C protein, rheumatoid factor, cryoglobulines, ASLO, fibrinogen.

In the case of dermatomyositis, carrying out the method according to the invention leads to complete rebuilding of the muscular system, alleviating the muscular, nervous and joint discomfort, extreme decreasing or withdrawal of corticosteroid therapy. In the same time, ASLO will be restored to normal values.

In the case of leukocytoclastic vasculitis, carrying out the method according to the invention leads to joint pain relieve, erythematous areas and related pains diminishing. Regarding the laboratory analyses, erythrocyte sedimentation rate and high fibrinogen level decreasing is noticed.

In the case of myasthenia gravis, carrying out the method according to the invention results in alleviating the phonation, mastication or deglutition difficulties and diplopia disappearance.

In the case of ulcer-hemorrhagic recto colitis, when the method according to the invention is applied, a normalizing of stool aspect, i.e. stool without blood, consistent, solid and colored, is detected.

In the case of chronic autoimmune hepatitis, applying the method according to the invention results in the normalizing of liver ultrasound aspect from nodular to normal liver, and from oversized to normally sized. Regarding the laboratory analyses, the following return to normal: transaminases, bilirubin, and electrophoresis.

Applying the method according to the invention is an important adjuvant for the AIDS treatment, through its immunity increasing and opportunistic infection induced inflammatory effect decreasing.

EXAMPLE 2

The process for manufacturing the IMUNOMOD active powder from the *Symphytum officinale* roots is identical to the one described in Example 1.

The ash obtained from the vegetal product calcination is dissolved in distilled water, in similar conditions to those in Example 1, and the obtained filtrate has the same composition.

The obtained filtrate is subjected to boiling evaporation in Pyrex glass recipients, up to a liquid viscousness of 6.57±0.5 cP. The viscid liquid thus obtained is placed on Pyrex pans, in thin layer, and is dried at 200-250° C., over a period of 5-10 minutes, thus obtaining an easy adhesive white powder. Right after the drying, the powder is detached using stainless tools known per se, and is introduced in tight flask, due to its great hygroscopic potential.

The IMUNOMOD active powder has the same composition as the one in Example 1.

In this Example for manufacturing the injectable solution according to the invention, the solution is designated to the administration in children with the same disorders as in adults.

For the injectable solution administration in 2-3 years old children, the IMUNOMOD active powder is formulated as a solution by its dissolving in distilled water, in amount of 150 mg to 100 ml distilled water, with an addition of 20 ml 1% Lidocaine solution. This solution is designated to fit in 2 ml ampules for intramuscular administration, and powder/ampoule concentration is given by the minimal dose for the 2-3 years old child/day/12 kg body weight, so the minimal daily dose would be a 2 ml ampoule, containing 7.5 mg active powder.

For the injectable solution administration, in 4-12 years old children, the IMUNOMOD active powder is formulated as a solution, by its dissolving in distilled water, in amount of 300 mg to 100 ml distilled water, with an addition of 20 ml of 1% Lidocaine solution. This solution is designated to fit in 2 ml ampules for intramuscular administration, and powder/ampoule concentration is given by the minimal dose for the 4-12 years old child/day/20 kg body weight, so the minimal dose would be a 2 ml ampoule, containing 15 mg active powder.

For children over 12 years of age, the injectable solution has the same active powder concentration as in adult case, noting that the unidose will be calculated on the body weight.

Intravenous administration in children should be performed only for those over 12 years of age, due to difficult manipulation of venous vessels, and to psychomotor stability increasing after this age. In these cases, the intravenous administration is also made slowly, over a period of 10 minutes. For the intravenous administration, the IMUNOMOD active powder is dissolved in saline solution, in amount of 100 mg to 100 ml saline solution, without Lidocaine addition. This solution is designated to fit in 15 ml ampoules for intravenous administration, active powder/ampoule concentration is of 30 mg active powder in 15 ml intravenous injectable solution and the unidose is also given by the body weight.

Thus obtained injectable and intramuscular administration designated solutions are fitted in ampules assigned for unidoses (2 ml for 2-12 years old children and 5 ml for children over 12 years of age) in aseptic medium are subjected to sterilization in the terms stipulated in Romanian Pharmacopeia, $X^{th}$ edition.

The injectable solutions for intravenous administration are fitted in 15 ml ampules as described in Example 1. Note that the intravenous administration of the injectable solution according to the invention is performed very slowly, over a period of minimum 10 minutes.

The method for treatment in children, in the case of chronic inflammatory disease, with the injectable solution according to the invention is similar to the one described in adult cases, noting that the intravenous administration is performed only in children over 12 years of age.

In the case of children less than 2 years of age, the solution according to the invention formulated at a concentration of 150 mg to 100 ml distilled water (without Lidocaine addition) may be orally administered at doses and by a method for treatment according to the present invention.

The method for treatment may be also applied in children with chronic autoimmune inflammatory diseases, for example nephrosis, rheumatoid arthritis, dermatomyositis, chronic autoimmune hepatitis.

In the case of nephrosis, the injectable solution administration according to the invention is highly effective. The administration is initially performed simultaneously with corticosteroid therapy, at least over a period of 10 days during the time the injectable solution according to the invention is administrated daily. In the second step of the method for treatment according to the invention, as soon as the positive effects occur (the edema retraction and the improvement of the α2-fraction level in electrophoresis), a slow decrease of the daily cortisone dose will be started, until the total cortisone excretion, over a period of about 3-4 months, during which the injectable solution is administrated weekly. At the end of the 4 months of treatment a notable edema retraction, along with the body weight loss, and electrophoresis correction are noticed, and after 11 months of maintenance treatment without corticosteroid therapy, the Cushing aspect completely disappears, and the height gain is notable.

In the case of arthritis, applying in children the method for treatment according to the invention results in joint tumefaction reduction, pain disappearance and normalizing the following analyses: ESR, reactive protein C, rheumatoid factor, cryoglobulines, ASLO, fibrinogen. The height gain is important and the visual deficit induced by the associated iridocyclitis, is considerably remitted.

In the case of chronic autoimmune hepatitis, applying the method according to the invention results in liver ultrasound aspect normalizing, from nodular to normal liver aspect, and from oversized to normally sized. Regarding the laboratory analyses, the following values return to normal: transaminases, bilirubin and electrophoresis.

The invention claimed is:

1. A method for producing an injectable solution, comprising the following steps:
   a) cutting and drying *Symphytum officinale* roots;
   b) calcination of the dried cut roots obtained in stage (a) at a temperature of 550-600° C., over a period of 3 to 4 hours to produce ash;
   c) dissolving the ash obtained after calcination in distilled water to produce a solution,
   d) filtering the obtained solution under vacuum, followed by additional filtration through Sempore filters and then through Millipore filters to produce a filtrate;
   e) drying the filtrate by boiling evaporation to produce a liquid having a high viscosity; and then further drying a thin layer of the high viscosity liquid at a temperature of 200-250° C., over a period of 5-15 minutes until a white powder is obtained; and
   f) dissolving the white powder in distilled water or a saline solution to produce injectable solution.

2. A method as claimed in claim 1 wherein lidocaine is incorporated in said injectable solution.

3. A method as claimed in claim 2 wherein lidocaine is incorporated in said injectable solution in an amount of from 0.1 to 0.2 mg per 100 ml of distilled water.

4. A method as claimed in claim 1 wherein the injectable solution produced comprises 1-700 mg of said white powder, and wherein the dissolved white powder contains water soluble inorganic salts, obtained from the ash resulting from calcination of *Symphytum officinale* roots , per 100 ml of the distilled water or saline solution.

5. A method as claimed in claim 4 wherein the dissolved white powder comprises 36-52% potassium salts and, stoichiometrically, comprises 43.268% potassium, 14.698% sulphur, 31.675% oxygen, 0.88% iron, 0.421% sodium, 0.265% phosphorus, 0.126% chlorine, 0.043% silicon, 0.034% magnesium, 0.012% manganese and cassiopeum traces, and up to 100% being carbon from carbonates and organic residues.

6. A method as claimed in claim 1 wherein hydrated potassium oxalate is incorporated in said injectable solution.

7. The method as claimed in claim 1 wherein the injectable solution obtained contains from 1 to 700 mg of dissolved solid per 100 ml of solution.

* * * * *

UNITED STATES PATENT AND TRADEMARK OFFICE
CERTIFICATE OF CORRECTION

PATENT NO. : 7,604,822 B2  Page 1 of 1
APPLICATION NO. : 10/381924
DATED : October 20, 2009
INVENTOR(S) : Elena Ionascu It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1574 days.

Signed and Sealed this

Fifth Day of October, 2010

David J. Kappos
*Director of the United States Patent and Trademark Office*